(12) United States Patent
Gao et al.

(10) Patent No.: US 10,245,227 B2
(45) Date of Patent: *Apr. 2, 2019

(54) SOFT, CHEWABLE AND ORALLY DISSOLVABLE AND/OR DISINTEGRABLE PRODUCTS

(71) Applicant: PHILIP MORRIS USA INC., Richmond, VA (US)

(72) Inventors: Feng Gao, Richmond, VA (US); Shalva Gedevanishvili, Richmond, VA (US); Shengsheng Liu, Richmond, VA (US); Munmaya K. Mishra, Manakin Sabot, VA (US); William R. Sweeney, Richmond, VA (US); Randall Baren, Glen Allen, VA (US); Qinglin Li, Richmond, VA (US); Darin Colassaco, Midlothian, VA (US); Salem Chouchane, Midlothian, VA (US)

(73) Assignee: Philip Morris USA Inc., Richmond, VA (US)

( * ) Notice: Subject to any disclaimer, the term of this patent is extended or adjusted under 35 U.S.C. 154(b) by 667 days.

This patent is subject to a terminal disclaimer.

(21) Appl. No.: 14/856,673

(22) Filed: Sep. 17, 2015

(65) Prior Publication Data

US 2016/0000708 A1   Jan. 7, 2016

Related U.S. Application Data

(62) Division of application No. 12/633,247, filed on Dec. 8, 2009, now Pat. No. 9,155,772.

(60) Provisional application No. 61/193,574, filed on Dec. 8, 2008.

(51) Int. Cl.

| | | |
|---|---|---|
| A61K 9/00 | (2006.01) |
| A61K 36/81 | (2006.01) |
| A61K 36/82 | (2006.01) |
| A23G 4/08 | (2006.01) |
| A23G 4/12 | (2006.01) |
| A23G 4/06 | (2006.01) |
| A24B 13/00 | (2006.01) |
| A24B 15/18 | (2006.01) |
| A24B 15/20 | (2006.01) |
| A61K 47/36 | (2006.01) |

(52) U.S. Cl.
CPC ............ *A61K 9/0056* (2013.01); *A23G 4/068* (2013.01); *A23G 4/08* (2013.01); *A23G 4/12* (2013.01); *A24B 13/00* (2013.01); *A24B 15/18* (2013.01); *A24B 15/20* (2013.01); *A61K 36/81* (2013.01); *A61K 36/82* (2013.01); *A61K 47/36* (2013.01); *A23V 2002/00* (2013.01)

(58) Field of Classification Search
CPC combination set(s) only.
See application file for complete search history.

(56) References Cited

U.S. PATENT DOCUMENTS

| | | |
|---|---|---|
| 865,026 A | 9/1907 | Ellis |
| 904,521 A | 11/1908 | Ellis |
| 1,376,586 A | 5/1921 | Schwartz |
| 3,132,651 A | 5/1964 | Kiefer |
| 3,747,608 A | 7/1973 | Gravely et al. |
| 3,974,838 A | 8/1976 | Mitchell et al. |
| 4,307,733 A | 12/1981 | Teng et al. |
| 4,317,837 A | 3/1982 | Kehoe et al. |
| 4,379,169 A | 4/1983 | Reggio et al. |
| 4,407,307 A | 10/1983 | Gaisch et al. |
| 4,476,881 A | 10/1984 | Gravely et al. |
| 4,537,204 A | 8/1985 | Gaisch et al. |
| 4,545,392 A | 10/1985 | Sensabaugh, Jr. et al. |
| 4,572,219 A | 2/1986 | Gaisch et al. |
| 4,606,357 A | 8/1986 | Dusek et al. |
| 4,624,269 A | 11/1986 | Story et al. |
| 4,709,710 A | 12/1987 | Gaisch et al. |
| 4,802,498 A | 2/1989 | Ogren |
| 4,887,618 A | 12/1989 | Bernasek et al. |
| 4,907,605 A | 3/1990 | Ray et al. |
| 4,917,161 A | 4/1990 | Townend |
| 4,941,484 A | 7/1990 | Clapp et al. |
| 5,092,352 A | 3/1992 | Sprinkle, III et al. |
| 5,327,917 A | 7/1994 | Lekwauwa et al. |
| 5,343,879 A | 9/1994 | Teague |
| 5,387,416 A | 2/1995 | White et al. |
| 5,482,722 A | 1/1996 | Cook |
| 5,601,097 A | 2/1997 | De Grandpre et al. |
| 5,740,016 A | 4/1998 | Dhindsa |
| 5,752,529 A | 5/1998 | Mane et al. |

(Continued)

FOREIGN PATENT DOCUMENTS

| | | |
|---|---|---|
| EP | 1148107 A1 | 10/2001 |
| WO | WO2006000233 | 1/2006 |

(Continued)

OTHER PUBLICATIONS

Decagon Devices "Fundamentals of Water Activity", 2006, 8 pages. (Year: 2006).*

*Primary Examiner* — Aaron J Kosar

(74) *Attorney, Agent, or Firm* — Buchanan Ingersoll & Rooney LLP

(57) ABSTRACT

A soft, chewable and orally dissolvable and/or disintegrable product includes a biopolymer-sugar based matrix and botanical powder dispersed throughout the biopolymer-sugar based matrix. The biopolymer-sugar based matrix includes at least one biopolymer, at least one sugar and optional additives. Soft, chewable and orally dissolvable and/or disintegrable product can also include flavor beads.

20 Claims, 1 Drawing Sheet

(56) References Cited

U.S. PATENT DOCUMENTS

| | | |
|---|---|---|
| 5,803,081 A | 9/1998 | O'Donnell, Jr. et al. |
| 6,194,008 B1 | 2/2001 | Li et al. |
| 6,571,801 B1 | 6/2003 | Wuolukka et al. |
| 6,613,363 B1 | 9/2003 | Li |
| 6,645,470 B1 | 11/2003 | Reynolds |
| 7,032,601 B2 | 4/2006 | Atchley et al. |
| 7,588,637 B2 | 9/2009 | Weisleder et al. |
| 8,124,147 B2 | 2/2012 | Chenq et al. |
| 8,356,606 B2 | 1/2013 | Sengupta et al. |
| 9,155,772 B2 * | 10/2015 | Gao .................. A61K 36/81 |
| 9,167,835 B2 * | 10/2015 | Sengupta ............. A23L 1/2205 |
| 9,351,936 B2 * | 5/2016 | Gao .................. A61K 9/2059 |
| 9,854,830 B2 * | 1/2018 | Gao .................. A24B 13/00 |
| 2004/0028772 A1 | 2/2004 | Andersen |
| 2004/0032036 A1 | 2/2004 | Subramaniam et al. |
| 2004/0101543 A1 | 5/2004 | Liu et al. |
| 2004/0118421 A1 | 6/2004 | Hodin et al. |
| 2004/0118422 A1 | 6/2004 | Lundin et al. |
| 2004/0182403 A1 | 9/2004 | Andersson et al. |
| 2005/0244521 A1 | 11/2005 | Strickland et al. |
| 2005/0244538 A1 | 11/2005 | Andersen et al. |
| 2006/0051455 A1 | 3/2006 | Andersen et al. |
| 2006/0099300 A1 | 5/2006 | Andersen et al. |
| 2006/0147498 A1 | 7/2006 | Jonsson et al. |
| 2006/0147580 A1 | 7/2006 | Nissen et al. |
| 2006/0191548 A1 | 8/2006 | Strickland et al. |
| 2007/0084476 A1 | 4/2007 | Yang et al. |
| 2007/0186942 A1 | 8/2007 | Strickland et al. |
| 2007/0186943 A1 | 8/2007 | Strickland et al. |
| 2007/0218179 A1 | 9/2007 | Ott et al. |
| 2008/0015264 A1 | 1/2008 | Schlelfenbaum et al. |
| 2008/0029117 A1 | 2/2008 | Mua et al. |
| 2009/0022856 A1 | 1/2009 | Cheng et al. |
| 2009/0133704 A1 | 5/2009 | Strickland et al. |
| 2010/0291245 A1 | 11/2010 | Gao et al. |

FOREIGN PATENT DOCUMENTS

| | | |
|---|---|---|
| WO | WO2006004480 A1 | 1/2006 |
| WO | WO2006065192 A1 | 6/2006 |

\* cited by examiner

SOFT, CHEWABLE AND ORALLY DISSOLVABLE AND/OR DISINTEGRABLE PRODUCTS

CROSS REFERENCE TO RELATED APPLICATIONS

This application is a divisional of U.S. application Ser. No. 12/633,247, filed Dec. 8, 2009, which claims priority to U.S. Provisional Application No. 61/193,574, filed Dec. 8, 2008, the entire content of each of which is hereby incorporated by reference.

SUMMARY

A soft, chewable and orally dissolvable and/or disintegrable product comprising a biopolymer-sugar based matrix and botanical powder in an amount sufficient to form at least about 30 wt % to about 75 wt % of the soft, chewable and orally dissolvable product is provided. The biopolymer-sugar based matrix comprises at least one biopolymer in an amount of about 1 to about 35 wt % of the soft, chewable and orally dissolvable product and at least one sugar in an amount of about 2 wt % to about 60 wt % of the soft, chewable and orally dissolvable and/or disintegrable product. The soft, chewable and orally dissolvable and/or disintegrable product is chewable in a user's mouth for about 3 minutes to about 10 minutes before dissolving and disintegrating in an oral cavity of a user. Also, the at least one sugar is included in an amount sufficient to substantially inhibit cross-linking between the at least one botanical powder and the at least one biopolymer.

In an embodiment, the soft, chewable and orally dissolvable and/or disintegrable product can also include flavor beads to add additional texture and flavor to the soft, chewable and orally dissolvable and/or disintegrable product. The flavor beads can include a polymer coating. The polymer coating can be abrasive. Preferably, the beads have diameters of about 0.5 mm to about 4.0 mm.

DETAILED DESCRIPTION

Figure 1:
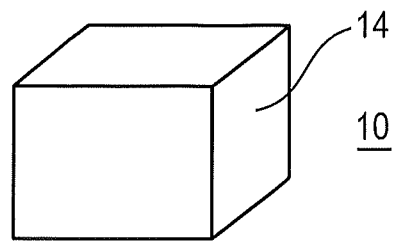
FIG. 1 is an illustration of an embodiment of a soft, chewable and orally dissolvable and/or disintegrable product comprising a biopolymer-sugar based matrix and botanical powder.

As shown in FIG. 1, a soft, chewable and orally dissolvable and/or disintegrable product 10 comprises a biopolymer-sugar based matrix and at least one botanical powder. Preferably, the biopolymer-sugar based matrix includes at least one biopolymer, which acts as a binder, and at least one sugar, which acts as a co-binder. In the preferred embodiment, the botanical powder is tobacco powder. Preferably, the soft, chewable and orally dissolvable and/or disintegrable product can be chewed by a user until substantially all of the ingredients contained therein substantially dissolve and disintegrate in the user's mouth.

In the preferred embodiment, the soft, chewable and orally dissolvable and/or disintegrable product 10 is free of animal products, such as gelatin. Preferably, animal products, such as gelatin, are not included in the matrix so as to prevent hardening of the matrix prior to use. In addition, by not including gelatin and/or other animal products, the soft, chewable and orally dissolvable and/or disintegrable product is acceptable for use by vegans, users with allergies, and/or users with cultural and religious beliefs, which discourage consumption of animal products. In addition, the lack of animal products in the soft, chewable and orally dissolvable and/or disintegrable product 10 prevents the transmission of possible diseases associated with animal tissues, such as bovine spongiform encephalopathy. In a preferred embodiment, the soft, chewable and orally dissolvable and/or disintegrable product 10 can also be organic.

In the preferred embodiment, the soft, chewable and orally dissolvable and/or disintegrable product does not include synthetic softeners, plasticizers or proteins (e.g., gelatin, rice protein, soy protein and/or corn zein). However, a softener and/or plasticizer, such as glycerin, can optionally be used to add additional softness to the biopolymer-sugar based matrix. Such softeners and/or plasticizers are unnecessary due to the use of the co-binder, which acts to inhibit cross-linking between the biopolymer binder and the botanical powder and resulting hardness.

As used herein, the terms "soft," "soften" and "softness" describes the soft, chewable and orally dissolvable and/or disintegrable product containing botanical powder in a relatively malleable state. Preferably, the product is firm, but not hard.

Preferably, the soft, chewable and orally dissolvable and/or disintegrable product 10 includes at least one biopolymer in an amount of about 1 wt % to about 35 wt %, more preferably about 2 wt % to about 20 wt % (e.g., about 2 wt % to about 5 wt %, about 5 wt % to about 10 wt %, about 10 wt % to about 15 wt % or about 15 wt % to about 20 wt %).

Suitable biopolymers include, without limitation, agar, alginate, carrageenans, such as iota carrageenan and kappa carrageenan, cellulose, gellan gum, guar gum, gum Arabic, konjac gum, locust bean gum, modified starch, pectin, xanthan gum, and/or combinations thereof. Preferably, the biopolymer does not comprise a protein, such as corn zein, rice protein, soy protein and/or gelatin.

In the preferred embodiment, the soft, chewable and orally dissolvable and/or disintegrable product 10 also includes a sugar. Preferably, the sugar provides both softening and sweetening of the soft, chewable and orally dissolvable and/or disintegrable product. Also preferably, the sugar is included in an amount of about 2 wt % to about 60 wt %, more preferably about 5 wt % to about 30 wt % (e.g., about 5 wt % to about 25 wt %, about 10 wt % to about 20 wt %, about 15 wt % to about 20 wt %, about 20 wt % to about 25 wt % or about 15 wt % to about 30 wt %).

In the preferred embodiment, the matrix does not harden even with prolonged exposure to air. Not wishing to be bound by theory, it is believed that the sugar forms hydrogen bonds with the biopolymer and blocks binding sites thereof to prevent cross-linking between the biopolymer and the botanical powder (e.g., tobacco, which is chemically active). By preventing cross-linking between the biopolymer and the tobacco, the soft, chewable and orally dissolvable and/or disintegrable product maintains a soft consistency as compared to oral products that contain cross-linked polymers.

Thus, if less than 2 wt % sugar is used, not all of the active sites of the biopolymer will be blocked, thereby allowing some cross-linking to occur, which results in the formation of a harder matrix. Alternatively, if sugar is used in larger amounts the active sites of the biopolymer will be completely blocked to form a soft product, and any excess sugar will act to sweeten the soft, chewable and orally dissolvable product.

Preferred sugars are small molecule saccharides, such as honey and/or high fructose corn syrup. However, other suitable sugars include, without limitation, monosaccharides (e.g., fructose, glucose, xylose, etc.), disaccharides (e.g., sucrose, trehalose, lactose, etc.), trisaccharides, polysaccharides, oligosaccharides (e.g., fructan and inulins), sugar alcohols (e.g., sorbitol, xylitol, lactitol, maltitol, etc.), and mixtures of sugars (e.g., combinations of honey, corn syrups, light corn syrups and/or high fructose corn syrups, etc.). Additionally, sweeteners, such as sucralose can be used.

Also preferably, the soft, chewable and orally dissolvable and/or disintegrable product 10 optionally includes at least one additive. Suitable additives include, without limitation, vitamins, minerals, nutraceuticals, energizing agents, soothing agents, coloring agents, amino acids, chemesthesis agents, antioxidants, flavorants, food grade emulsifiers, pH modifiers, and/or combinations thereof. The additives can be included in the soft, chewable and orally dissolvable product 10 in an amount of up to about 10 wt % (e.g., about 1 wt % to about 5 wt % or about 5 wt % to about 10 wt %).

Suitable soothing agents include, without limitation, chamomile, lavender, jasmine, and the like.

Suitable energizing ingredients include, without limitation, caffeine, taurine, and guarana.

Suitable vitamins include, without limitation, vitamin A (retinol), vitamin D (cholecalciferol), vitamin E group, vitamin K group (phylloquinones and menaquinones), thiamine (vitamin $B_1$), riboflavin (vitamin $B_2$), niacin, niacinamide, pyridoxine (vitamin $B_6$ group), folic acid, choline, inositol, vitamin $B_{12}$ (cobalamins), PABA (para-aminobezoic acid), biotin, vitamin C (ascorbic acid), and mixtures thereof. The amount of vitamins incorporated into soft, chewable and orally dissolvable and/or disintegrable product can be varied according to the type of vitamin and the intended user of the soft, chewable and orally dissolvable and/or disintegrable product. For example, the amount of vitamins may be formulated to include an amount less than or equal to the recommendations of the United States Department of Agriculture Recommended Daily Allowances.

The chemesthesis ingredients can provide, without limitation, hot, spicy, or cooling flavors. Suitable chemesthesis agents include, without limitation, capsaicin, tannins, mustard oil, wintergreen oil, cinnamon oil, allicin, quinine, citric acid, and salt.

As used herein, the term "nutraceuticals" refers to any ingredient in foods that has a beneficial effect on human health. Nutraceuticals include particular compounds/compositions isolated from natural food sources and genetically modified food sources. For example, nutraceuticals include various phytonutrients derived from natural plants and genetically engineered plants.

Suitable minerals include, without limitation, calcium, magnesium, phosphorus, iron, zinc, iodine, selenium, potassium, copper, manganese, molybdenum, chromium, and mixtures thereof. The amount of minerals incorporated into the soft, chewable and orally dissolvable and/or disintegrable product can be varied according to the type of vitamin and the intended user. For example, the amount of minerals may be formulated to include an amount less than or equal to the recommendations of the United States Department of Agriculture Recommended Daily Allowances.

Suitable amino acids include, without limitation, the eight essential amino acids that cannot be biosynthetically produced in humans, including valine, leucine, isoleucine, lysine, threonine, tryptophan, methionine, and phenylalanine. Examples of suitable amino acids include the non-essential amino acids including alanine, arginine, asparagine, aspartic acid, cysteine, glutamic acid, glutamine, glycine, histidine, proline, serine, and tyrosine.

In another embodiment, the soft, chewable and orally dissolvable and/or disintegrable product 10 can include various active agents having antioxidant properties that can delay the ageing process, as food-grade ingredients. For example, the active ingredients that can be extracted from *Ginkgo biloba* include flavonoid glycosides ("ginkgoflavonoids"), such as (iso)quercitin, kaempferol, kaempferol-3-rhamnosides, isorhamnetin, luteolin, luteolin glycosides, sitosterol glycosides, and hexacyclic terpene lactones, referred to as "ginkgolides" or "bilobalides." The active ingredients that can be extracted from *Camellia sinensis*, such as green tea, include various "tea tannins," such as epicatechol, epigallocatechol, epigallocatechol gallate, epigallocatechol gallate, theaflavin, theaflavin monogallate A or B, and theaflavin digallate. The active ingredients that can be extracted from *Vaccinium myrtillus*, such as blueberry, include at least 15 different anthocyanosides, such as delphinidin, anthocyanosides, myrtin, epimyrtin, phenolic acids, glycosides, quercitrin, isoquercitrin, and hyperoside. The active ingredients that can be extracted from *Vinis vitifera*, such as grapes, include polyphenols, catechols, quercitrins, and resveratrols. The active ingredients that can be extracted from *Olea europensis*, such as the leaves of olive trees, include oleuropein. Many active ingredients identified from these and other plant sources associated with the neutralization of free radicals and useful for delaying the ageing process are contemplated. Other antioxidants known in the art are also contemplated.

The active ingredients of *Trifolium pratense*, such as purple clovers (i.e., common purple trefoils), include isoflavones or isoflavone glucosides, daidzein, genestein, formononentin, biochanin A, ononin, and sissostrin. The health-promoting properties of compounds derived from *Panax*, a genus that includes Ginseng, are well-established. These and other botanicals, botanical extracts, and bioactive compounds having health promoting effects are contemplated.

The botanical extracts may be prepared by various methods known in the art, including maceration, remaceration, digestion, agitation maceration, vortex extraction, ultrasonic extraction, countercurrent extraction, percolation, repercolation, evacolation, diacolation, and solid/liquid extraction under continuous reflux.

Suitable flavorants include any flavorants commonly used in foods, confections, oral products and/or tobacco articles. Exemplary flavorants include, but are not limited to, berry flavors such as pomegranate, acai, raspberry, blueberry, strawberry, boysenberry, and/or cranberry. Other suitable flavorants include, without limitation, any natural or synthetic flavor or aroma, such as menthol, peppermint, spearmint, wintergreen, bourbon, scotch, whiskey, cognac, hydrangea, lavender, chocolate, licorice, citrus and other fruit flavors, such as apple, peach, pear, cherry, plum, orange, lime, grape, and grapefruit, gamma octalactone, vanillin, ethyl vanillin, breath freshener flavors, butter, rum, coconut, almond, pecan, walnut, hazelnut, French vanilla, macadamia, sugar cane, maple, cassis, caramel, banana, malt, espresso, kahlua, white chocolate, spice flavors such as cinnamon, clove, cilantro, basil, oregano, garlic, mustard, nutmeg, rosemary, thyme, tarragon, dill, sage, anise, and fennel, methyl salicylate, linalool, jasmine, coffee, olive oil, sesame oil, sunflower oil, bergamot oil, geranium oil, lemon oil, ginger oil, balsamic vinegar, rice wine vinegar, and red wine vinegar.

The flavorants can be incorporated in the matrix or applied to the soft, chewable and orally dissolvable and/or disintegrable product 10 by spraying, coating, immersing, embossing, and/or dispersing them into or onto the soft, chewable and orally dissolvable product itself. In an embodiment, the flavorants are added in the form of spray dried flavorants, essential oils, and/or solutions. In other embodiments, the flavorants can be added to the biopolymer solution during formation of the soft, chewable and orally dissolvable product.

Suitable pH modifiers include, without limitation, $Na_2CO_3$, $NaHCO_3$, $K_3PO_4$, $K_3HPO_4$, NaOH, HCl, citric acid and combinations thereof. pH modifiers can be added to adjust the flavor of the soft, chewable and orally dissolvable and/or disintegrable product 10. Since some polymers tend to be acidic by nature, a pH modifier can be included to neutralize the taste of the soft, chewable and orally dissolvable product 10. Preferably, the soft, chewable and orally dissolvable and/or disintegrable product 10 has a pH of about 5 to about 8, more preferably about 7 to about 8. A pH less than about 5 tends to be too sour.

In an embodiment, the soft, chewable and orally dissolvable and/or disintegrable product 10 can include a food-grade emulsifier. Preferably, the food-grade emulsifier is added when oil based flavorants, such as wintergreen oil, are included in the soft, chewable and orally dissolvable product 10 to stabilize the flavorant within the hydrocolloid based matrix. Typically, food-grade emulsifiers are not necessary for use with water based flavorants. However, food-grade emulsifiers can be used with water based flavorants if desired. Suitable food-grade emulsifiers include, without limitation, phospholipids, such as lecithins, fatty acid mono- and di-glycerides, phosphated monoglycerides, glycerol esters, such as glycerol monooleate, glycerol monotallate, polyglycerol oleate and/or polyglycerol decaoleate, sorbitan esters, such as sorbitan monolaurate, sorbitan monostearate, sorbitan monooleate and/or sorbitan trioleate, and/or polysorbates (e.g., Polysorbate 20 and/or Polysorbate 80).

In the preferred embodiment, the soft, chewable and orally dissolvable and/or disintegrable product 10 includes at least one botanical powder in an amount of up to about 75 wt % by weight based on the weight of the soft, chewable and orally dissolvable product, more preferably about 30 wt % to about 75 wt % (e.g., about 45 wt % to about 55 wt %, about 55 wt % to about 65 wt % or about 65 wt % to about 75 wt %). Preferably, if tobacco powder is used, the tobacco powder is included in an amount of at least about 50 wt %. Suitable botanical powders can include tea powder, tobacco powder, coffee powder, herbal powders, spice powders and/or combinations thereof. Preferably, the botanical powder is derived from any botanical material that has a surface chemistry with functional groups (e.g., phenolics) that cross-link proteins and biopolymers. Also preferably, the soft, chewable and orally dissolvable and/or disintegrable product 10 includes a majority amount of the botanical powder to increase flavor delivery thereof. In a preferred embodiment, the botanical material disintegrates in the user's mouth.

As used herein, the term "botanical powder" describes dust, fines, colloidal dispersions, granules, dried botanical extract and the like having dimensions of less than about 50 mesh, more preferably less than about 200 mesh and most preferably less than about 400 mesh. In an embodiment, the soft, chewable and orally dissolvable product 10 can also include botanical extracts as described above. The botanical powder can be ground for inclusion in the soft, chewable and orally dissolvable product 10 or the botanical powder can be scrap dust and fines too small for inclusion in other products. The smaller the botanical powder, the less gritty the soft, chewable and orally dissolvable and/or disintegrable product may feel in a user's mouth. In addition, the use of smaller botanical powders results in faster disintegration of the powders.

In the preferred embodiment, the botanical powder is tobacco powder. For example, tobacco can be ground to produce a powder for incorporation in the soft, chewable and orally dissolvable and/or disintegrable product 10. Examples of suitable types of tobacco materials that can be used in the soft, chewable and orally dissolvable product 10 include, but are not limited to, flue-cured tobacco, air-cured, Burley tobacco, Maryland tobacco, Oriental tobacco, rare tobacco, specialty tobacco, blends thereof and the like. The tobacco material may be provided in any suitable form, including, but not limited to, tobacco extract powders, tobacco lamina, processed tobacco materials such as volume expanded or puffed tobacco, aged tobacco, processed tobacco stems, such as cut-rolled or cut-puffed stems, reconstituted tobacco materials, tobacco root, stem and/or stalk material, blends thereof, and the like. The tobacco may also be genetically modified tobacco or tobacco having a reduced tobacco specific nitrosamine (TSNA) content.

In a preferred embodiment, the tobacco can be enzyme treated tobacco, such as, without limitation, the enzyme treated tobacco described in U.S. Pat. No. 4,941,484, U.S. Pat. No. 4,887,618, U.S. Pat. No. 4,307,733, U.S. Pat. No. 3,974,838, U.S. Pat. No. 3,747,608, U.S. Pat. No. 4,407,307 and commonly owned U.S. Pat. No. 4,307,733, filed on Dec. 17, 1979, the entire contents of which are incorporated herein by reference.

In an embodiment, ground tobacco powder is dispersed in water and then treated with up to about 5 wt % enzyme, more preferably up to about 4 wt % enzyme by dispersing tobacco powder in water to form a suspension, adding at least one enzyme to the suspension, storing the suspension at about 45° C. for about 24 hours to about 60 hours to form enzyme treated tobacco and adding the enzyme treated tobacco to a biopolymer-sugar based matrix. In a preferred embodiment, the tobacco powder is treated with up to about 0.6 wt % enzyme. Suitable enzymes include, without limitation, pectinases, cellulases, hemicellulases, ferulic acid esterase, proteases, lipases and combinations thereof. In an embodiment, commercially available enzyme solutions can be used to treat the tobacco. In a preferred embodiment, the tobacco powder is treated with a combination of enzymes. In an embodiment, the soft, chewable and orally dissolvable and/or disintegrable product can include enzyme treated tobacco alone or in combination with other types of tobacco and/or botanical materials.

The following examples of methods of preparing enzyme treating tobacco and incorporating enzyme treated tobacco in soft, chewable and orally dissolvable and/or disintegrable product are exemplary and are not meant to limit any aspects of the embodiments disclosed herein.

Example 1

About 4 g of tobacco powder having dimensions of less than about 400 mesh are dispersed in about 400 ml water at about 45° C. to form a suspension. Less than about 0.6 wt % enzyme is added to the suspension. The suspension is stored at about 45° C. for about 60 hours to complete enzyme treatment. After treatment, a biopolymer binder and sugar co-binder can be added at about 90° C. and cooked for about 20 minutes to form a mixture. The mixture can be gelled at about 4° C. for about 2 hours and then dried at about 55° C. for about 12 hours to form a soft, chewable and orally dissolvable and/or disintegrable product including enzyme treated tobacco.

Example 2

About 4 g of tobacco powder having dimensions of less than about 400 mesh are dispersed in about 400 ml water at about 45° C. to form a suspension. Less than about 0.6 wt % enzyme is added to the suspension. The suspension is stored at about 45° C. for about 24 hours to complete enzyme treatment. After treatment, a biopolymer binder and sugar co-binder can be added at about 90° C. and cooked for about 20 minutes to form a mixture. The mixture can be gelled at about 4° C. for about 2 hours and then dried at about 55° C. for about 12 hours to form a soft, chewable and orally dissolvable and/or disintegrable product including enzyme treated tobacco.

Example 3

About 4 g of tobacco powder, including a 1:1 ratio of dark air cured tobacco and stems, having dimensions of less than about 400 mesh are dispersed in about 400 ml water at about 45° C. to form a suspension. Less than about 0.6 wt % enzyme is added to the suspension. The suspension is stored at about 45° C. for about 60 hours to complete enzyme treatment. After treatment, a biopolymer binder and sugar co-binder can be added at about 90° C. and cooked for about 20 minutes to form a mixture. The mixture can be gelled at about 4° C. for about 2 hours and then dried at about 55° C. for about 12 hours to form a soft, chewable and orally dissolvable and/or disintegrable product including enzyme treated tobacco.

Not wishing to be bound by theory, it is believed that the use of enzyme treated tobaccos in the soft, chewable and orally dissolvable and/or disintegrable product 10 may aid in softening and/or modifying the texture of the soft, chewable and orally dissolvable and/or disintegrable product because the enzymes used to treat the tobacco are believed to break down cell walls of the tobacco. In addition, it is believed that the use of enzyme treated tobacco in soft, chewable and orally dissolvable and/or disintegrable product aids in enhancing the texture of the products, which also have low water activity levels. The enzyme treatment may also aid in the disintegration of the tobacco is a user's mouth.

In an embodiment, if the soft, chewable and orally dissolvable and/or disintegrable product 10 includes tobacco powder, the orally dissolvable product 10 can also include at least one non-tobacco flavorant. However, soft, chewable and orally dissolvable and/or disintegrable product 10 including tobacco powder and/or other botanical powders can also include tobacco based or non-tobacco based flavorants.

Preferably, about 0.01 mg to about 100 mg of a flavorant is added to the soft, chewable and orally dissolvable and/or disintegrable product 10. The amount of flavorant added can depend on the type and/or potency of the flavorant being added, but is preferably added in an amount of up to about 15 wt %, more preferably up to about 10 wt %. In an embodiment, the soft, chewable and orally dissolvable and/or disintegrable product 10 can include multiple flavorants.

For example, a preferred soft, chewable and orally dissolvable and/or disintegrable product 10 can comprise about 50 wt % tobacco powder, about 20% biopolymer binder, about 20 wt % sugar co-binder, about 3 wt % flavorant and sweeteners and about 7 wt % other additives including enzymes used to treat the tobacco powder.

In the preferred embodiment, the soft, chewable and orally dissolvable and/or disintegrable product 10 is formed by first forming a solution of water, the biopolymer binder and the sugar co-binder while stirring at about 90° C. The botanical powder and/or other additives can then be added to the solution to form a homogenous mixture. Preferably, the botanical powder does not come into contact with the biopolymer binder before the biopolymer binder and sugar co-binder are mixed so as to inhibit cross-linking between the botanical powder and the biopolymer binder. The mixture can then be cast and allowed to gel at about 4° C. to about 10° C. for about 30 minutes to about 12 hours to form a gel.

Once the gel is formed, the gel can be dried to adjust the water content. In a preferred embodiment, the soft, chewable and orally dissolvable and/or disintegrable product 10 also has a low water activity of about 0.70 $a_w$ to about 0.30 $a_w$, and more preferably less than about 0.60 $a_w$. The oven volatiles content of the final soft, chewable and orally dissolvable and/or disintegrable product is about 10 wt % to about 16 wt %. The low water content of the soft, chewable and orally dissolvable and/or disintegrable product 10 protects against microbial growth in the product thereby increasing shelf-life. Preferably, the water content is adjusted by drying the soft, chewable and orally dissolvable and/or disintegrable product after formation as described below.

Preferably, the shelf-life of the soft, chewable and orally dissolvable and/or disintegrable product 10 is at least about 2 weeks, more preferably at least about 2 months and most preferably at least about 4 months (e.g., at least about 6 months). Despite the low moisture content, the soft, chewable and orally dissolvable and/or disintegrable product could theoretically still suffer from chemical oxidation and/or loss of flavor. Thus, the shelf-life may be increased and/or decreased based on the ingredients of the soft, chewable and orally dissolvable and/or disintegrable product and changes therein over time.

Since the soft, chewable and orally dissolvable and/or disintegrable product 10 includes a minor amount of water, some hardening may take place over time due to drying. However, because the water content is so low, the hardening resulting from drying is substantially unnoticeable to consumers. In other embodiments, additional water can be added to increase plasticity of the soft, chewable and orally dissolvable and/or disintegrable product 10 if desired. However, additional water may cause noticeable hardening due to drying and shorter shelf-life.

In the embodiment, the soft, chewable and orally dissolvable and/or disintegrable product that is formed as described above can be dried at room temperature for about 1 hours to about 72 hours. In other embodiments, the gel can be dried in an oven at about 50° C. to about 80° C., preferably about 60° C. for about 1 hours to about 72 hours, preferably about 12 hours to about 36 hours.

In a preferred embodiment, the soft, chewable and orally dissolvable and/or disintegrable product 10 is cut into shapes and/or molded before and/or after gelation to form suitably sized, pre-portioned pieces of soft, chewable and orally dissolvable and/or disintegrable product 10. In an embodiment, the product can be extruded.

The following are not meant to limit any aspects of the embodiments disclosed herein.

Example 4

To form a soft, chewable and orally dissolvable and/or disintegrable product containing tobacco powder, up to about 10 wt % Glycerol Monooleate, about 2 wt % to about 20 wt % carrageenan and about 5 wt % to about 30 wt % honey are dissolved in water at about 90° C. while stirring to form a mixture. Then up to about 10 wt % baking soda and up to about 60 wt % 400 mesh ground tobacco powder is added to the mixture. After homogenous dispersion is obtained, up to about 10 wt % of additional flavorant is added. The mixture is then cast on a polyethylene tray. The mixture is then gelled at about 5° C. for about 2 hours, and dried at about 60° C. for about 36 hours. The dried sample is cut into desired shapes to form the soft, chewable and orally dissolvable and/or disintegrable product.

In the preferred embodiment, the soft, chewable and orally dissolvable and/or disintegrable product containing tobacco powder can be placed in a user's mouth and chewed for about 30 seconds to about 40 minutes, more preferably about 4 minutes to about 8 minutes depending on the size and composition. After chewing, the soft, chewable and orally dissolvable and/or disintegrable product dissolves in the mouth.

Also preferably, soft, chewable and orally dissolvable and/or disintegrable products comprising tobacco powder may have a rubbery texture when chewed, prior to dissolution, as compared to soft, chewable and orally dissolvable and/or disintegrable products comprising other botanical powders.

Example 5

To form a soft, chewable and orally dissolvable and/or disintegrable product containing tea powder, up to about 10 wt % food grade emulsifier, up to about 30 wt % carrageenan, up to about 30 wt % modified starch, and up to about 30 wt % honey are dissolved in water at about 90° C. while stirring to form a mixture. Then, up to about 30 wt % tea extract powder is added to the mixture. After a homogenous dispersion is obtained, up to about 10 wt % of an additional flavorant is added to the mixture. The mixture is then cast on a polyethylene tray. The mixture is gelled at about 5° C. for about 2 hours and then dried at about 60° C. overnight. The dried sample is cut into the desired shapes to form the soft, chewable and orally dissolvable and/or disintegrable product.

In a preferred embodiment, soft, chewable and orally dissolvable and/or disintegrable product 10 including tea powder can be chewed for about 30 seconds to about 40 minutes, more preferably about 5 minutes to about 10 minutes depending on the size and composition. Also preferably, after drying, the water activity is about 0.60 $a_w$ to about 0.30 $a_w$. The soft, chewable and orally dissolvable and/or disintegrable product 10 containing tea powder is chewy and/or gummy in texture and dissolves in a user's mouth after chewing.

Example 6

About 2 g pectin and about 4 g honey are dissolved in about 100 ml of water at about 95° C. to form a solution. About 5 g tobacco powder is added to the solution while stirring for about 10 minutes to form a suspension. The suspension is then cast on a sterile polyethylene tray and gelled at about 5° C. for about 2 hours. The gel is then dried overnight at about 40° C. to form a dried gel. The dried gel is then cut into desired shapes and sizes to form pre-portioned soft, chewable and orally dissolvable and/or disintegrable products.

Example 7

About 2 g gellan gum and about 4 g high fructose corn syrup are dissolved in about 100 ml of water at about 95° C. to form a solution. About 5 g tobacco powder is added to the solution while stirring for about 10 minutes to form a suspension. The suspension is then cast on a sterile polyethylene tray and gelled at about 5° C. for about 2 hours. The gel is then dried overnight at about 40° C. to form a dried gel. The dried gel is then cut into desired shapes and sizes to form pre-portioned soft, chewable and orally dissolvable and/or disintegrable products.

Example 8

About 2 g xanthan gum and about 4 g honey are dissolved in about 100 ml of water at about 95° C. to form a solution. About 5 g tobacco powder is added to the solution while stirring for about 10 minutes to form a suspension. The suspension is then cast on a sterile polyethylene tray and gelled at about 5° C. for about 2 hours. The gel is then dried overnight at about 40° C. to form a dried gel. The dried gel is then cut into desired shapes and sizes to form pre-portioned soft, chewable and orally dissolvable and/or disintegrable products.

Example 9

About 2 g modified starch and about 4 g honey are dissolved in about 100 ml of water at about 95° C. to form a solution. About 5 g tobacco powder is added to the solution while stirring for about 10 minutes to form a suspension. The suspension is then cast on a sterile polyethylene tray and gelled at about 5° C. for about 2 hours. The gel is then dried overnight at about 40° C. to form a dried gel. The dried gel is then cut into desired shapes and sizes to form pre-portioned soft, chewable and orally dissolvable and/or disintegrable products.

Example 10

About 2 g xanthan gum and about 4 g honey are dissolved in about 100 ml of water at about 95° C. to form a solution. About 5 g tea powder is added to the solution while stirring for about 10 minutes to form a suspension. The suspension is then cast on a sterile polyethylene tray and gelled at about 5° C. for about 2 hours. The gel is then dried overnight at about 40° C. to form a dried gel. The dried gel is then cut into desired shapes and sizes to form pre-portioned soft, chewable and orally dissolvable and/or disintegrable products.

Example 11

About 2 g carrageenan and about 4 g high fructose corn syrup are dissolved in about 100 ml of water at about 95° C. to form a solution. About 5 g tea powder is added to the solution while stirring for about 10 minutes to form a suspension. The suspension is then cast on a sterile polyethylene tray and gelled at about 5° C. for about 2 hours. The gel is then dried overnight at about 40° C. to form a dried gel. The dried gel is then cut into desired shapes and sizes to form pre-portioned soft, chewable and orally dissolvable and/or disintegrable products.

Example 12

About 2 g pectin and about 4 g honey are dissolved in about 100 ml of water at about 95° C. to form a solution. About 5 g tea powder is added to the solution while stirring for about 10 minutes to form a suspension. The suspension is then cast on a sterile polyethylene tray and gelled at about 5° C. for about 2 hours. The gel is then dried overnight at about 40° C. to form a dried gel. The dried gel is then cut into desired shapes and sizes to form pre-portioned soft, chewable and orally dissolvable and/or disintegrable products.

Example 13

About 2 g modified starch and about 4 g honey are dissolved in about 100 ml of water at about 95° C. to form a solution. About 5 g tea powder is added to the solution while stirring for about 10 minutes to form a suspension. The suspension is then cast on a sterile polyethylene tray and gelled at about 5° C. for about 2 hours. The gel is then dried overnight at about 40° C. to form a dried sample. The dried gel is then cut into desired shapes and sizes to form pre-portioned soft, chewable and orally dissolvable and/or disintegrable products.

In a preferred embodiment, the soft, chewable and orally dissolvable and/or disintegrable product 10 is pre-portioned to create individual pieces of the soft, chewable and orally dissolvable and/or disintegrable product for packaging and shipping to the consumer. Preferably, each pre-portioned piece of the soft, chewable and orally dissolvable and/or disintegrable product 10 is sized and configured to fit comfortably in the user's mouth. Also preferably, if the soft, chewable and orally dissolvable and/or disintegrable product 10 has edges, the edges are soft edges. Suitably sized pieces can be packaged individually for distribution to consumers. Alternatively, multiple pieces can be placed in a single package for distribution to consumers.

The soft, chewable and orally dissolvable and/or disintegrable product 10 may be formed in many shapes including, without limitation, spheres, rectangles, oblong shapes, crescent shapes, star shapes, leaf shapes, fruit shapes, ovals, and cubes. The shape of the soft, chewable and orally dissolvable and/or disintegrable product 10 can indicate the type of botanical powder and/or flavorant included in the soft, chewable and orally dissolvable and/or disintegrable product 10. For example, a tea leaf shape could indicate that tea powder is incorporated in the soft, chewable and orally dissolvable and/or disintegrable product.

In a preferred embodiment, the soft, chewable and orally dissolvable and/or disintegrable product is pre-portioned, rectangular in shape and weighs about 0.5 g to 4.0 g, more preferably about 1.0 g to about 3.0 g. The pre-portioned soft, chewable and orally dissolvable and/or disintegrable product 10 may be up to about 2 inches long, up to 2 inches in height, and up to 2 inches in width. More preferably, the pre-portioned soft, chewable and orally dissolvable and/or disintegrable product 10 is up to about 1 inch long, up to about 1 inch in height and up to about 1 inch in width. Most preferably, the pre-portioned soft, chewable and orally dissolvable and/or disintegrable product 10 ranges from about 0.1 inch to about 1.5 inch long, about 0.1 inch to about 1.5 inch in height and about 0.1 inch to about 1.5 inch in width.

Preferably, the soft, chewable and orally dissolvable and/or disintegrable product 10 is chewable for about 30 seconds to about 40 minutes, more preferably about 3 minutes to about 20 minutes and most preferably about 4 minutes to about 10 minutes in a user's mouth. The chewing time can vary depending on the formulation (e.g., type and amount of botanical powder, biopolymer binder and/or sugar co-binder used) and size of the soft, chewable and orally dissolvable and/or disintegrable product 10. For example, larger pieces of the soft, chewable and orally dissolvable and/or disintegrable product 10 can be chewed for a longer period of time than smaller pieces of the soft, chewable and orally dissolvable and/or disintegrable product 10. After chewing, the soft, chewable and orally dissolvable and/or disintegrable product 10 dissolves and/or disintegrates in the user's mouth and is swallowed. In an embodiment, the biopolymer and sugar dissolve and the botanical powder disintegrates. In other embodiments, all components of the product can dissolve and/or disintegrate. In an embodiment, the chewing speeds up dissolution and disintegration in a user's mouth.

In the preferred embodiment, the density of the soft, chewable and orally dissolvable and/or disintegrable product 10 is less than about 2.0 g/cm$^3$, more preferably less than about 0.9 g/cm$^3$. In an embodiment, the soft, chewable and orally dissolvable and/or disintegrable product 10 can be aerated, if desired, to lower the density of the soft, chewable and orally dissolvable and/or disintegrable product as compared to non-aerated embodiments of the soft, chewable and orally dissolvable and/or disintegrable product 10.

Figure 2:
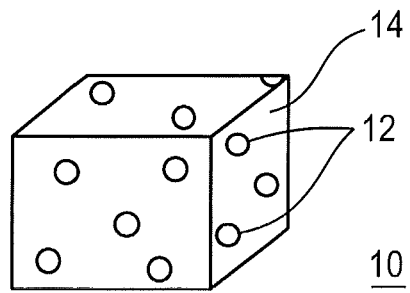
FIG. 2 is an illustration of an embodiment of a soft, chewable and orally dissolvable and/or disintegrable product comprising a biopolymer-sugar based matrix, a botanical powder and flavor beads.
Figure 3:
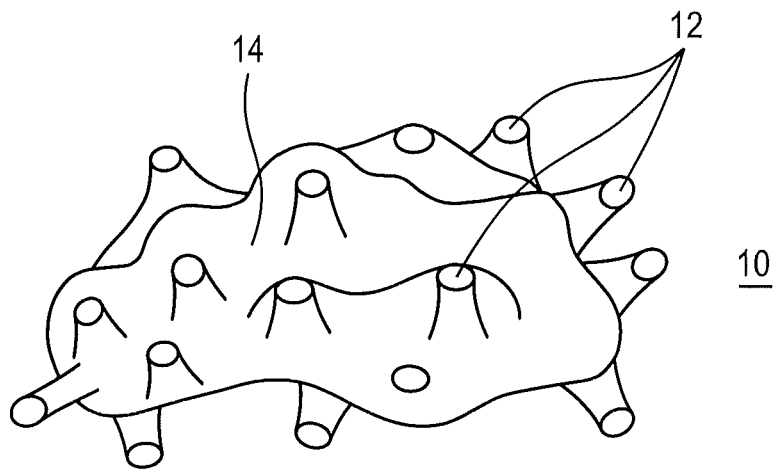
FIG. 3 is an illustration of an embodiment of a soft, chewable and orally dissolvable and/or disintegrable product comprising a biopolymer-sugar based matrix, a botanical powder and flavor beads.

In another embodiment, as shown in FIGS. 2 and 3, the soft, chewable and orally dissolvable and/or disintegrable product 10 can comprise a biopolymer-sugar based matrix 14, botanical powder and flavor beads 12. The flavor beads 12 can provide a different texture to the soft, chewable and orally dissolvable and/or disintegrable product 10. The flavor beads 12 can include encapsulated flavorants, other additives and/or botanicals. Preferably, the flavor beads 12 include tobacco. The flavor beads 12 can have a solid, liquid or gel center with a hard exterior coating. The coating can be cross-linked or non-cross-linked, and can include one or more polymers. Preferably, if the biopolymer-sugar based matrix 14 does not include animal products and/or animal byproducts, the flavor beads 12 also do not include animal products.

In an embodiment, the coating of the flavor beads 12 can be roughened so as to provide an abrasive surface that can rub and/or clean the teeth during chewing.

Preferably, the flavor beads 12 are substantially spherical and have diameters of ranging from about 0.5 mm to about 4.0 mm, more preferably about 0.5 mm to about 3.0 mm. Flavor beads 12 included in an individual soft, chewable and orally dissolvable and/or disintegrable product can have the same size or an individual soft, chewable and orally dissolvable and/or disintegrable product can include flavor beads of different sizes.

Also, the flavor beads 12 can be randomly and/or uniformly distributed throughout the biopolymer-sugar based matrix 14. In an embodiment, the flavor beads 12 can be placed only in the center of the biopolymer-sugar based matrix 14 or only on the exterior of the biopolymer-sugar based matrix 14. In other embodiments, the flavor beads 12 can be arranged in a pattern within the biopolymer-sugar based matrix 14. For example, one the homogenous mixture is placed in a mold, flavor beads can be arranged as desired in and/or on the soft, chewable and orally dissolvable and/or disintegrable product 10.

The flavor beads 12 provide the soft, chewable and orally dissolvable and/or disintegrable product 10 with a crunchy texture when chewed. In an embodiment, the beads 12 can be popped by mechanical action during chewing. The mechanical action can aid in the release of the filling material of the flavor beads 12. Thus, the crunchy texture provides additional oral activities to the user such that the user can chew, suck and/or crunch the soft, chewable and orally dissolvable and/or disintegrable product and the flavor beads 12 contained therein.

Alternatively, the flavor beads 12 can dissolve in the user's mouth if not popped, such that the filling material of the flavor beads 12 is not released until the coating dissolves. In a preferred embodiment, the flavor beads 12 completely disintegrate and/or dissolve after chewing along with the soft, chewable and orally dissolvable and/or disintegrable product 10 such that nothing remains in the user's mouth after use that must be removed and discarded.

Suitable flavor beads 12 can be formed via polysaccharide coating, protein-polysaccharide coacervation, extrusion and/or spheronization, and/or other methods as described below. In an embodiment, tobacco and/or other botanicals can be encapsulated as in U.S. patent application Ser. No. 12/155,227, filed on May 30, 2008, the entire content of which is incorporated herein by reference. If tobacco is encapsulated in the beads, the soft, chewable and orally dissolvable and/or disintegrable product 10 can include tobacco in an amount above 75 wt %.

In an embodiment, the flavor beads 12 can include controlled release mechanisms such as pH change, heat activation, or mechanical activation through manipulating and/or sucking. In addition, flavor beads 12 can have encapsulating coatings of various thicknesses so that the flavorants are released at varying rates to provide continuous or different flavor throughout use of the soft, chewable and orally dissolvable and/or disintegrable product 10. In an embodiment, the dissolution time of the matrix 14 and/or flavor beads 12 can be altered by changing the polysaccharides and mixtures thereof used within the soft, chewable and orally dissolvable and/or disintegrable product 10. For example, the rate of dissolution can be increased by using polysaccharides that are more readily soluble in saliva, while the rate of dissolution can be slowed by using polysaccharides that are less soluble in saliva.

In an embodiment, the soft, chewable and orally dissolvable and/or disintegrable product 10 can include flavor beads 12 of multiple flavorants so that the user is provided with at least two flavors during consumption. In addition, when using flavor beads 12 of varying flavors within the same soft, chewable and orally dissolvable and/or disintegrable product 10, the first flavor bead 12 and the second flavor bead 12 may be released by the same or different mechanisms at the same or different times. Additional flavor beads 12 having the same and/or different flavors may also be used, and may be triggered by different methods at different times.

In one embodiment, complimentary flavors beads 12 may be chosen for different time release flavorants to provide a combined flavor. For instance, a cherry vanilla flavor may be provided by choosing a cherry flavor bead 12 and a vanilla flavor bead 12. In an embodiment, the release of flavorants from the cherry flavor bead 12 and the vanilla flavor bead 12 can overlap so that the complimentary flavorants can be enjoyed together.

In addition to providing flavors and texture, the use of flavor beads 12 allows for even higher botanical loading in the final soft, chewable and orally dissolvable and/or disintegrable product when the flavor beads 12 incorporate botanical materials. Since the botanicals are encapsulated, harsh flavors are avoided as the encapsulated botanicals release the botanicals over the duration of the chewing time rather than all at once.

In this specification, the word "about" is often used in connection with numerical values to indicate that mathematical precision of such values is not intended. Accordingly, it is intended that where "about" is used with a numerical value, a tolerance of ±10% is contemplated for that numerical value.

While the foregoing describes in detail an soft, chewable and orally dissolvable and/or disintegrable product that is chewable, dissolvable and disintegrable in the oral cavity with reference to specific embodiments thereof, it will be apparent to one skilled in the art that various changes and modifications equivalents to the soft, chewable and orally dissolvable and/or disintegrable product and process steps may be employed, which do not materially depart from the spirit and scope of the invention. Accordingly, all such changes, modifications, and equivalents that fall within the spirit and scope of the invention as defined by the appended claims are intended to be encompassed thereby.

We claim:

1. A method of making a pre-portioned, soft, chewable and orally-dissolvable and/or -disintegrable product comprising:
   dissolving a biopolymer and a sugar in water to form a solution;
   adding an amount of a botanical powder to the solution;
   stirring the solution to form a suspension;
   gelling the suspension to form a gel;
   drying the gel to form a dried gel; and
   portioning the dried gel to form a pre-portioned, soft, chewable and orally-dissolvable and/or -disintegrable product, wherein
   the amount of the botanical powder is distributed in a biopolymer-sugar based matrix.

2. The method of claim 1, wherein the solution is heated to a temperature of about 40° C. to about 95° C. and wherein the solution is stirred for about 15 minutes to about 45 minutes.

3. The method of claim 1, wherein the soft, chewable and orally dissolvable and/or disintegrable product comprises about 30 wt % to about 75 wt % of the botanical powder, about 1 wt % to about 35 wt % of the biopolymer, about 2 wt % to about 60 wt % of the sugar and up to about 10 wt % additives.

4. The method of claim 1, wherein the sugar is included in an amount sufficient to substantially inhibit cross-linking between the botanical powder and the biopolymer.

5. The method of claim 1, wherein:
   the sugar is selected from the group consisting of:
      monosaccharides including fructose, glucose and xylose; disaccharides including sucrose, trehalose and lactose;
      trisaccharides;
      polysaccharides;
      oligosaccharides including fructan and inulins;
      sugar alcohols including sorbitol, xylitol, lactitol and maltitol; and
      combinations thereof;
   the biopolymer is selected from the group consisting of gellan gum, konjac gum, modified starch, pectin, carrageenan, guar gum, xanthan gum, locust bean gum, agar, gum Arabic, alginate, cellulose and combinations thereof;

the botanical powder is selected from the group consisting of tobacco powder, coffee powder, tea powder, herb powder, spice powder, cocoa powder and combinations thereof; and the botanical powder has dimensions of less than about 50 mesh.

6. The method of claim 1, wherein the botanical powder has dimensions of less than about 50 mesh.

7. The method of claim 1, wherein the soft, chewable and orally-dissolvable and/or -disintegrable product is up to about 1 inch in height, up to about 1 inch in width, and up to about 1 inch in length and wherein the soft, chewable and orally-dissolvable and/or -disintegrable product has a density of less than about 2.0 g/cm$^3$.

8. The method of claim 1, wherein the soft, chewable and orally-dissolvable and/or -disintegrable product ranges in size from about 0.1 inch to about 0.5 inch in height, about 0.5 inch to about 1.0 inch in width and about 0.25 to about 0.5 inch in length.

9. The method of claim 1, wherein the soft, chewable and orally-dissolvable and/or -disintegrable product further comprises (a) at least one vitamin, (b) at least one mineral, (c) at least one nutraceutical, (d) at least one amino acid, (e) at least one energizing agent, (f) at least one soothing agent, (g) at least one sweetener, (h) at least one coloring agent, (i) at least one chemesthesis agent, (j) at least one antioxidant, (k) at least one food-grade emulsifier and/or (l) at least one pH modifier.

10. The method of claim 1, wherein the soft, chewable and orally-dissolvable and/or -disintegrable product has a water activity of about 0.70 $a_w$ to about 0.30 $a_w$.

11. The method of claim 1, wherein the soft, chewable and orally-dissolvable and/or -disintegrable product has water activity of less than about 0.60 $a_w$.

12. The method of claim 1, wherein the sugar is selected from the group consisting of:
monosaccharides including fructose, glucose and xylose;
disaccharides including sucrose, trehalose and lactose;
trisaccharides;
polysaccharides;
oligosaccharides including fructan and inulins;
sugar alcohols including sorbitol, xylitol, lactitol and maltitol; and
combinations thereof.

13. The method of claim 1, wherein the biopolymer is selected from the group consisting of agar, alginate, carrageenan, cellulose, gellan gum, guar gum, gum Arabic, konjac gum, locust bean gum, modified starch, pectin, xanthan gum, and combinations thereof.

14. The method of claim 1, wherein the pre-portioned, soft, chewable and orally-dissolvable and/or -disintegrable product includes flavor beads comprising a solid, liquid or gel center and a hard outer coating.

15. The method of claim 14, wherein the pre-portioned, soft, chewable and orally-dissolvable and/or -disintegrable product includes a hard outer coating comprising a polymeric coating.

16. The method of claim 15, wherein the hard outer coating has a rough surface.

17. The method of claim 14, wherein the flavor beads are included in the soft, chewable and orally-dissolvable and/or -disintegrable product in an amount of about 1 wt % to about 5 wt % based on the weight of the soft, chewable and orally dissolvable and/or disintegrable product.

18. The method of claim 14, wherein the flavor beads are contained in a center of the soft, chewable and orally-dissolvable and/or -disintegrable product and/or on the exterior of the soft, chewable and orally dissolvable and/or disintegrable product.

19. A method of making a soft, chewable and orally-dissolvable and/or -disintegrable product comprising:
dispersing tobacco powder in water to form a suspension;
adding at least one enzyme in an amount of up to about 5 wt % by weight of the tobacco powder to the suspension;
storing the suspension at a temperature above about 35° C. for about 24 hours to about 60 hours to form enzyme treated tobacco;
dissolving a biopolymer and a sugar in water to form a solution;
adding the enzyme treated tobacco to the solution;
stirring the solution to form a suspension;
gelling the suspension to form a gel;
drying the gel to form a dried gel; and
portioning the dried gel to form a pre-portioned, soft, chewable and orally-dissolvable and/or -disintegrable product.

20. The method of claim 19, wherein the enzyme is selected from the group consisting of pectinases, cellulases, hemicellulases, ferulic acid esterase, proteases, lipases and combinations thereof.

* * * * *